US009916657B2

(12) United States Patent
Choi (10) Patent No.: US 9,916,657 B2
(45) Date of Patent: Mar. 13, 2018

(54) METHOD AND DEVICE FOR RESTORING SCAN IMAGE AND RECORDING MEDIUM FOR STORING SAME (71) Applicants: Vatech Co., Ltd., Gyeonggi-do (KR); Vatech Ewoo Holdings Co., Ltd., Gyeonggi-do (KR)

(72) Inventor: Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 34 days.

(21) Appl. No.: 14/913,686

(22) PCT Filed: Aug. 20, 2014

(86) PCT No.: PCT/KR2014/007740
§ 371 (c)(1),
(2) Date: Feb. 22, 2016

(87) PCT Pub. No.: WO2015/026164
PCT Pub. Date: Feb. 26, 2015

(65) Prior Publication Data
US 2016/0203601 A1    Jul. 14, 2016

(30) Foreign Application Priority Data
Aug. 20, 2013 (KR) .................. 10-2013-0098311

(51) Int. Cl.
G06K 9/00 (2006.01)
A61B 6/00 (2006.01)
(Continued)

(52) U.S. Cl.
CPC .......... G06T 7/0012 (2013.01); A61B 5/7257 (2013.01); A61B 6/5205 (2013.01);
(Continued)

(58) Field of Classification Search
CPC ............... A61B 6/00; G06K 9/00; G06T 7/00
(Continued)

(56) References Cited

U.S. PATENT DOCUMENTS 8,008,642 B2 * 8/2011 Schweizer ............ G01T 1/2012
250/591
8,938,111 B2 * 1/2015 Kingston ............... A61B 6/032
128/922
(Continued)

FOREIGN PATENT DOCUMENTS

EP      1492050 A2   12/2004
WO  2008/050320 A2    5/2008

OTHER PUBLICATIONS

Soyoung Lee et al., "Image Restoration Simulation of Digital X-ray Images Based upon Filtering Techniques and the Quality Evaluation of the Restored Images", Journal of the Korean Society of Radiology, Dec. 2008, pp. 33-40, vol. 2, No. 4.
(Continued)

Primary Examiner — Abolfazl Tabatabai
(74) Attorney, Agent, or Firm — IP Legal Services, LLC (57) ABSTRACT Disclosed is a method for restoring a scan image. The method includes the steps of: measuring a blurring function oversampled with respect to a slit image obtained through a slit inclined at a predetermined angle in a vertical or horizontal direction according to the predetermined angle; and restoring a scan image to increase a resolution of an interface of a subject in the scan image obtained by obtaining the subject using the measured blurring function. Computed tomography (CT) that applies image restoration by increasing sampling can secure a precise image for computer-aided design (CAD)/computer-aided manufacturing (CAM) addi-
(Continued)

tionally used in a system used when actually diagnosing a patient, and thus does not require additional expenses and equipment.

12 Claims, 6 Drawing Sheets

(51) Int. Cl.
| | |
|---|---|
| *G06T 7/00* | (2017.01) |
| *A61B 5/00* | (2006.01) |
| *G06T 3/40* | (2006.01) |
| *G06T 5/00* | (2006.01) |
| *G06T 11/00* | (2006.01) |
| *A61B 5/05* | (2006.01) |
| *A61B 6/03* | (2006.01) |

(52) U.S. Cl.
CPC .......... *G06T 3/4007* (2013.01); *G06T 3/4084* (2013.01); *G06T 5/002* (2013.01); *G06T 5/003* (2013.01); *G06T 11/006* (2013.01); *A61B 6/032* (2013.01); *G06T 2207/10072* (2013.01); *G06T 2207/10081* (2013.01); *G06T 2207/10116* (2013.01)

(58) Field of Classification Search
USPC ............ 382/128–134; 378/4, 8, 21–27, 901; 600/407, 410, 411, 425, 427
See application file for complete search history.

(56) References Cited

U.S. PATENT DOCUMENTS

| | | | |
|---|---|---|---|
| 9,217,687 B2 * | 12/2015 | Orband | .............. G01M 11/0207 |
| 2004/0246347 A1 | 12/2004 | Nokita | |
| 2009/0067742 A1 | 3/2009 | Lim et al. | |
| 2010/0080487 A1 | 4/2010 | Yitzhaky et al. | |

OTHER PUBLICATIONS

Akihiro Kayugawa et al., "Accurate determination of CT point-spread-function with high precision", Journal of Applied Clinical Medical Physics, Jan. 2013, pp. 216-226, vol. 14, No. 4.

Hiroshi Fujita et al., "A Simple Method for Determining the Modulation Transfer Function in Digital Radiography", IEEE Transactions on Medical Imaging, Mar. 1, 1992, pp. 34-39, vol. 11, No. 1, IEEE Service Center, Piscataway, NJ, US.

Cyril Ponchut et al., "Experimental Comparison of Pixel Detector Arrays and CCD-Based Systems for X-Ray Area Detection on Synchrotron Beamlines", 2004 IEEE Nuclear Science Symposium Conference Record, Oct. 16, 2004, pp. 4676-4680, vol. 7.

Jan-Jakob Sonke et al., "Focal spot motion of linear accelerators and its effect on portal image analysis", Medical Physics, Jun. 1, 2003, pp. 1067-1075, vol. 30, No. 6.

* cited by examiner

FIG. 12

METHOD AND DEVICE FOR RESTORING SCAN IMAGE AND RECORDING MEDIUM FOR STORING SAME

CROSS REFERENCE TO RELATED APPLICATIONS

This application is a National Stage Patent Application of PCT International Patent Application No. PCT/KR2014/007740 (filed on Aug. 20, 2014) under 35 U.S.C. § 371, which claims priority to Korean Patent Application No. 10-2013-0098311 (filed on Aug. 20, 2013), the teachings of which are incorporated herein in their entireties by reference.

TECHNICAL FIELD

The present invention relates generally to a method for restoring a scan image and, more particularly to a method for restoring a scan image to find a position of an interface of a subject.

BACKGROUND ART

In existing computed tomography (CT) reconstruction images, positions of area to be reconstructed are reconstructed using sampling data of an image acquired by a sensor, and thereby interface information about oversampling, etc., limited to a size of one pixel that is unique to the sensor, is minimally expressed.

In image systems using X-rays, an image is blurred due to several principles that are necessary in the process of acquiring the image, and a reconstruction image using the blurred image is also limited to its resolution.

A blurring model of this image system is expressed by Equation 1. A subject of an original shape passes through the image system, and the image system outputs a final result influenced by its characteristic function, noise, and so on.

$$g(x,y)=h(x,y)*f(x,y) \quad \text{Equation 1}$$

Here, f(x,y) indicates an amount of light of an original image at x and y-axial coordinates (x, y), h(x,y) is a point spread function as a blurring function, and g(x,y) indicates an amount of light of a blurred original image.

Figure 2:
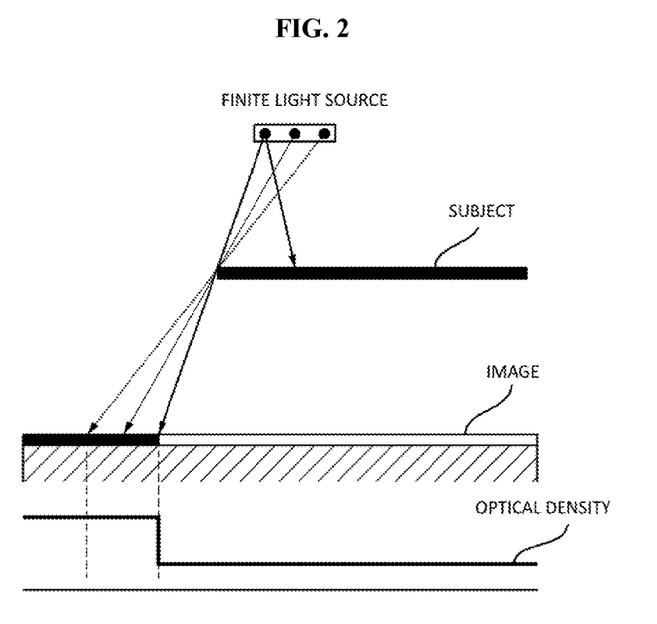

This blurring function produces an effect of blurring an interface of the subject as in FIG. 2 due to a penumbral effect caused by a size of a focal point, and has an effect of fundamentally reducing and limiting a resolution of the sensor and a resolution of the image ahead of the other limitations.

DISCLOSURE

Technical Problem

Accordingly, the present invention has been made keeping in mind the above problems occurring in the prior art, and an object of the present invention is to provide an algorithm capable of extracting a focal point occurring at an image system and another blurring function to accurately express an original interface of a subject.

Technical Solution

In order to accomplish the above object, a method for restoring a scan image according to the present invention includes the steps of: measuring a blurring function oversampled with respect to a slit image obtained through a slit inclined at a predetermined angle in a vertical or horizontal direction according to the predetermined angle; and restoring the scan image to increase a resolution of an interface of a subject in the scan image obtained by obtaining the subject using the measured blurring function.

The step of measuring the blurring function may include the sub-steps of: generating line spread functions (LSFs) with respect to a plurality of alignments composed of digital values sampled with respect to the slit image according to a pixel interval of the image; and measuring a modulation transfer function (MTF) as the blurring function of the slit image using the plurality of LSFs.

The step of restoring the scan image may include the sub-steps of: interpolating the scan image to correspond to an oversampling interval of the slit image; and restoring the interpolated scan image using the measured blurring function.

The step of measuring the blurring function may further include the sub-step of synthesizing the plurality of generated LSFs according to the angle and the pixel interval of the slit image to generate a synthesized LSF, and the sub-step of measuring the MTF may include measuring the MTF using the synthesized LSF.

The sub-step of generating the synthesized LSF may include synthesizing and generating the plurality of LSFs according to an interval obtained by dividing the pixel interval by the number (N) of the pixels between the plurality of alignments.

The sub-step of measuring the MTF may include transforming the LSFs to optical transfer functions (OTFs) using Fourier transform, and measuring the MTF using the transformed OTFs.

The measured MTF may be an absolute value of the transformed OTF.

The step of restoring the scan image may include the sub-step of limiting a frequency of the subject to a frequency of a boundary portion including the interface of the subject to restore the scan image.

The scan image may be a computed tomography (CT) scan image acquired by CT, and the method of restoring the scan image further includes the step of reconstructing the scan image to a CT image.

The method may further include the step of calculating surface data by detection of the interface from the reconstructed CT image.

The angle of the slit inclined in the vertical or horizontal direction may range from 2 to 3°.

In order to accomplish the above object, a device for restoring a scan image includes: a blurring function measurement unit configured to measure a blurring function oversampled with respect to a slit image obtained through a slit inclined at a predetermined angle in a vertical or horizontal direction according to the predetermined angle; an image restoration unit configured to restore the scan image to increase a resolution of an interface of a subject in the scan image obtained by obtaining the subject using the measured blurring function.

The blurring function measurement unit may include: a line spread function (LSF) generation part configured to generate LSFs with respect to a plurality of alignments composed of digital values sampled with respect to the slit image according to a pixel interval of the image; and a modulation transfer function (MTF) measurement part configured to measure an MTF as the blurring function of the slit image using the plurality of LSFs.

The image restoration unit may include: an image interpolation part configured to interpolate the scan image to correspond to an oversampling interval of the slit image; and an interpolated image restoration part configured to restore the interpolated scan image using the measured blurring function.

The blurring function measurement unit may further include a synthesized LSF generation part configured to synthesize the plurality of generated LSFs according to the angle and the pixel interval of the slit image to generate a synthesized LSF, and the MTF measurement part may measure the MTF using the synthesized LSF.

The synthesized LSF generation part may synthesize and generate the plurality of LSFs according to an interval obtained by dividing the pixel interval by the number (N) of the pixels between the plurality of alignments.

The MTF measurement part may transform the LSFs to optical transfer functions (OTFs) using Fourier transform, and measure the MTF using the transformed OTFs.

The measured MTF may be an absolute value of the transformed OTF.

The image restoration unit may limit a frequency of the subject to a frequency of a boundary portion including the interface of the subject to restore the scan image.

The scan image may be a computed tomography (CT) scan image acquired by CT, and the device of restoring the scan image may further include an image reconstruction unit configured to reconstruct the scan image to a CT image.

The device may further include a surface data calculation unit configured to calculate surface data by detecting the interface from the reconstructed CT image.

The angle of the slit inclined in the vertical or horizontal direction may range from 2 to 3°.

In order to accomplish the above object, a program that executes the method for restoring the scan image according to the present embodiment on a computer includes the steps of: measuring a blurring function oversampled with respect to a slit image obtained through a slit inclined at a predetermined angle in a vertical or horizontal direction according to the predetermined angle; and restoring the scan image to increase a resolution of an interface of a subject in the scan image obtained by obtaining the subject using the measured blurring function.

Advantageous Effects

In general, the CT equipment for diagnosis uses a generator having a focal point of about 0.5 mm. This generator is positively necessary to secure a sufficient amount of tube current for acquiring an image of a patient. When there is a need to express a high-resolution interface, a micro-focus generator is used. In this case, the CT equipment is expensive, and cannot be used due to an excessive exposure dose or a deficient tube current when additionally obtaining the patient.

The CT that applies the image restoration by increasing the sampling can secure a precise image for computer-aided design (CAD)/computer-aided manufacturing (CAM) additionally used in a system used when actually diagnosing the patient, and thus does not require additional expenses and equipment.

MODE FOR INVENTION

The following description merely exemplifies the principle of the present invention. Thus, although not explicitly described or shown in this disclosure, various devices in which the principle of the present invention is implemented and which are encompassed in the concept or scope of the present invention can be invented by one of ordinary skill in the art. It should be appreciated that all the conditional terms enumerated herein and embodiments are clearly intended only for a better understanding of the concept of the present invention, and the present invention is not limited to the particularly described embodiments and statuses.

The forgoing objects, advantages and features of invention will become more readily apparent from the following detailed description taken in conjunction with the accompanying drawings, and accordingly, one of ordinary skill in the art may easily practice the embodiment of the present invention. Further, in the description of the present invention, when it is determined that the detailed description of the related art would obscure the subject matter of the present invention, the description thereof will be omitted. Hereinafter, preferred embodiments of the present invention will be described in detail with reference to the drawings.

In existing computed tomography (CT) reconstruction images, positions of areas to be reconstructed are reconstructed using sampling data of an image acquired by a sensor, and thereby information about an oversampling interface, limited to a size of one pixel that is unique to the sensor, is minimally expressed.

In image systems using X-rays, an image is actually blurred due to several principles that are necessary in the process of acquiring the image, and a reconstruction image using the blurred image is also limited to its resolution.

Figure 1:
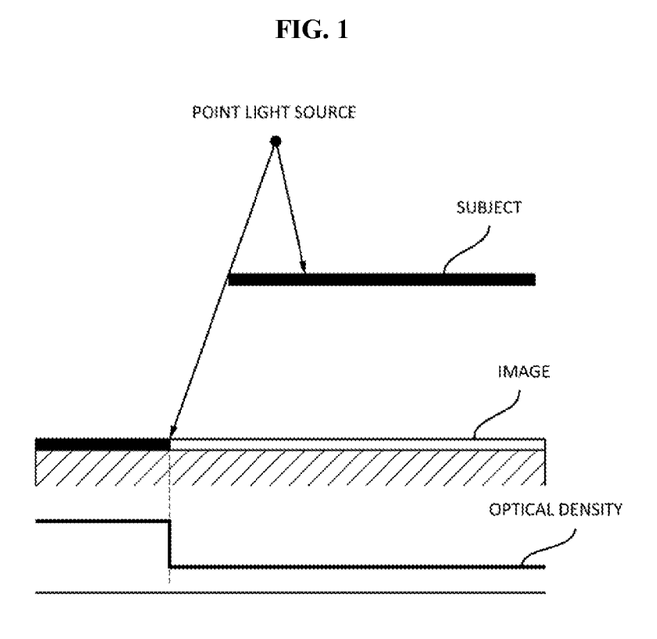
FIGS. 1 and 2 are views illustrating generation of a blur phenomenon in a process of sampling an image acquired at a sensor of the present invention.

A subject of an original shape passes through the image system, and the image system outputs a final result influenced by its characteristic function, noise, and so on. Referring to FIG. 1, in the case of the image system having a point light source, the final result shows a distinct difference in optical density at the interface of the subject, and thus the interface can be accurately detected. Typically, in the case of the image system having a finite light source, there occurs a phenomenon in which the interface of the subject is blurred as in FIG. 2 due to a penumbral effect caused by a size of a focal point, and a resolution of the sensor and a resolution of the image ahead of the other limitations are fundamentally reduced and limited.

Figure 3:
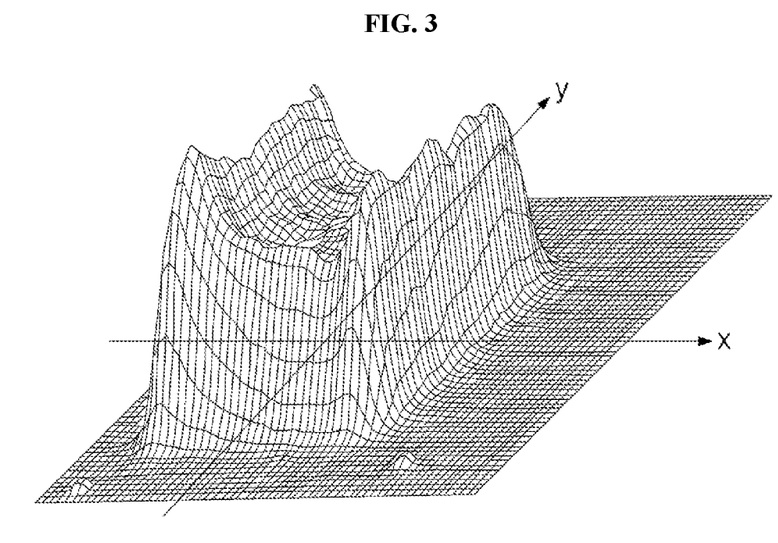
FIG. 3 is a view illustrating a size of a focal point in an image system according to the present invention.
Figure 4:
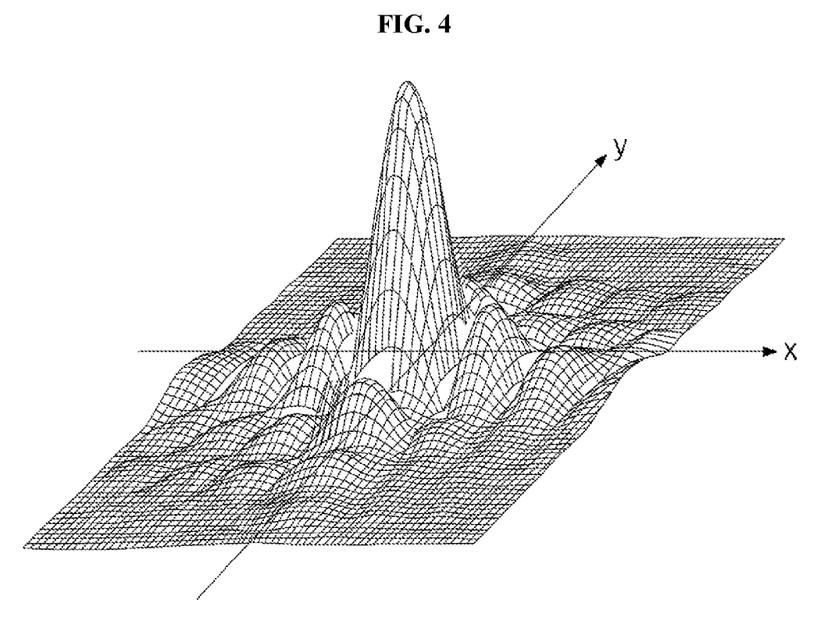
FIG. 4 is a view illustrating a result of a modulation transfer function (MTF) when the image of FIG. 3 is subjected to Fourier transform.

The size of the focal point has a specific size as in FIG. 3, and can be measured. Further, distribution in an amount of light of the focal point is represented by a modulation transfer function (MTF) as in FIG. 4.

Hereinafter, a method for restoring a scan image according to an embodiment of the present invention will be described with reference to FIGS. 5 to 9.

Figure 5:
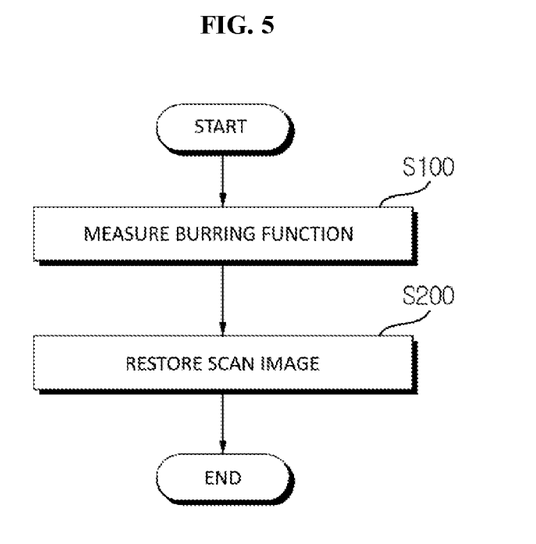
FIG. 5 is a flow chart illustrating a method for restoring a scan image according to an embodiment of the present invention.

Referring to FIG. 5, the method for restoring a scan image in the present embodiment includes a blurring function measuring step S100 and a scan image restoring step S200.

In the blurring function measuring step S100, a blurring function oversampled according to a predetermined angle is measured for a slit image obtained through a slit that is vertically or horizontally inclined at the predetermined angle. The slit image is an image obtained by adjusting a slit having a fine width and alignment of an X-ray tube. In the present embodiment, a slit having a fine width of preferably 10 μm is obtained by adjustment of alignment along with rotation or leftward/rightward movement. Further, an angle at which the slit is inclined vertically or horizontally is determined for oversampling to be described below. In the present embodiment, it is preferable to use a slit that is vertically inclined at an angle of 2 to 3°, and more preferably 2.54°.

Further, in the present embodiment, the oversampling refers to securing a sampling interval wider than that of an actually acquired image to express a resolution that is equal to or higher than that of the image limited to the size of the focal size and that of the image limited to the size of the pixel. Therefore, it is possible to include information about an error, etc. caused by the sampling interval occurring when an actual image is acquired. In the image system using X-rays as in Equation 1 above, the image is blurred due to the several principles that are necessary in the process of acquiring the image, and the reconstruction image using the blurred image is also limited to the resolution. The blurring function is a function in which a blur of the original image is expressed in a mathematical relationship in the blurring model of the image system expressed as in Equation 1. Hereinafter, measurement of the blurring function in the present embodiment will be described in greater detail with reference to FIG. 6.

Figure 6:
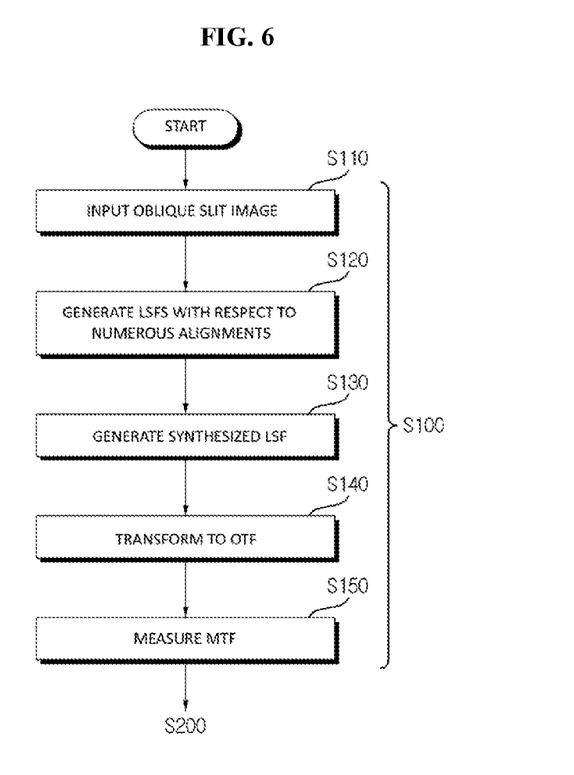
FIGS. 6 and 7 are detailed flow charts of the method for restoring the scan image of FIG. 5.

Referring to FIG. 6, the measurement of the blurring function in the present embodiment may carried out by a step S110 of receiving the inclined slit image, a step S120 of producing line spread functions (LSFs) for a plurality of alignments, a step S130 of producing a synthesized LSF, a step S140 of transforming an optical transfer function (OTF), and a step S150 of measuring an MTF.

In the step S120 of producing the LSFs for the plurality of alignments, the LSFs for the plurality of alignments are sampled using the slit image received in the step S110 of receiving the slit image according to the pixel interval of the slit image, and are composed of digital values.

Figure 8:
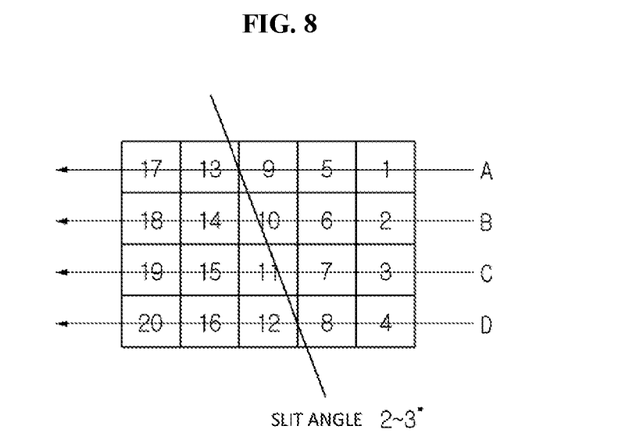
FIG. 8 is a view illustrating alignments of a slit image according to the embodiment of the present invention.

Referring to FIG. 8, there are four alignments A, B, C and D with respect to the slit image inclined at an angle of 2 to 3°. Therefore, in the step S120, four LSFs composed of five digital values are produced for four alignments using a pixel interval Δx as the sampling interval.

In the step S130 of producing the synthesized LSF, the produced LSFs are synthesized according to the angle of the slit image and the pixel interval, and the synthesized LSF is produced.

In the step S130 of producing the synthesized LSF, the plurality of LSFs are preferably synthesized according to an interval obtained by dividing the pixel interval by the number N of pixels between the plurality of alignments.

Figure 9:
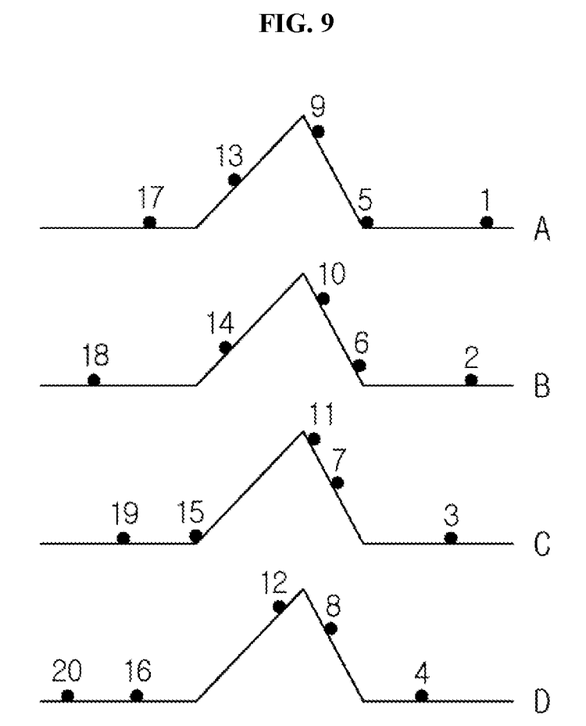
FIG. 9 is a view illustrating a line spread function (LSF) of each alignment of FIG. 8.
Figure 10:
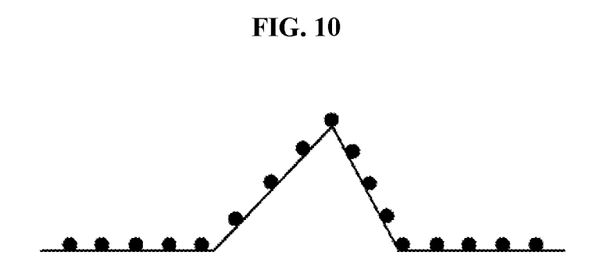
FIG. 10 is a view illustrated a synthesized LSF generated by synthesizing the LSFs of FIG. 9.

Therefore, in FIG. 8, since there are four alignments for one pixel, when a total of 20 data are synthesized at a sampling interval of Δx/4, and a synthesized LSF in which the sampling interval is small is produced. FIG. 9 schematically illustrates LSFs corresponding to respective alignments. Numbers provided for each LSF are identification numbers representing the synthesis order. When result values of the LSFs are synthesized at a sampling interval of Δx/4 in ascending order of number, a final synthesized LSF as illustrated in FIG. 10 is produced. Hereinafter, the step S140 of transforming the OTF will be described. Prior to measuring the MTF, the LSF is transformed to the OTF. In the present embodiment, the transformation of the LSF to the OTF is performed using Fourier transform, and is expressed as in Equation 2.

$$\text{OTF}(\mu) = \int_{-\infty}^{\infty} \text{LSF}(x) e^{-i2\pi\mu x} \quad \text{Equation 2}$$

Here, LSF(x) is the synthesized LSF produced in the step S130 of producing the synthesized LSF, and OTF(μ) is a result formula of the Fourier transform of the synthesized LSF. Further, μ is a spatial frequency, and δμ is a phase.

Furthermore, Equation 2 is expressed as Equation 3 by Euler's formula.

$$A - iB = |\text{OTF}(\mu)|_e^{-i\delta\mu x} \quad \text{Equation 3}$$

Here, $A = \int \text{LSF}(x)\cos(2\pi\mu x)dx$ and $B = \int \text{LSF}(x)\sin(2\pi\mu x)dx$ In the step S150 of measuring the MTF, the MTF is measured using the transformed OTF. The MTF is measured with the absolute value of the transformed OTF.

Here, the scan image restoring step S200 using the measured MTF in the present embodiment will be described in greater detail with reference to FIG. 7.

Figure 7:
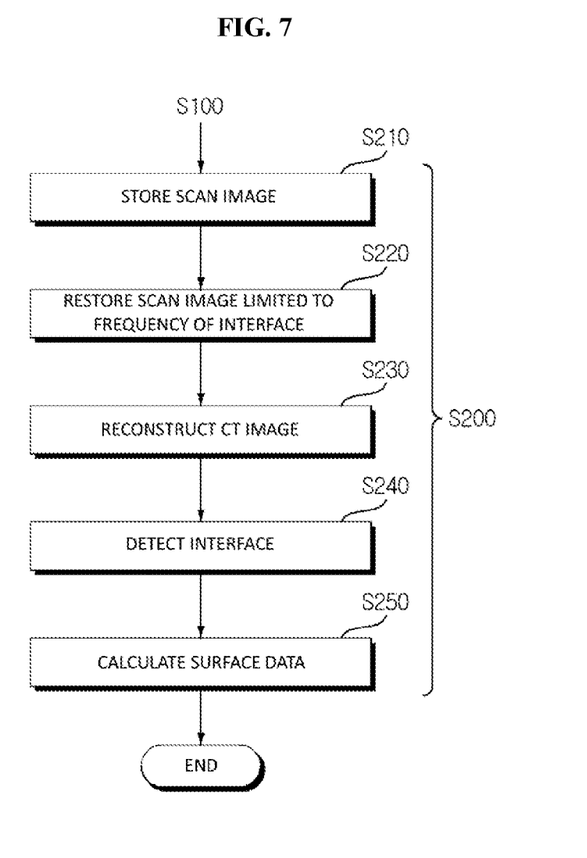

Referring to FIG. 7, the scan image restoring step S200 of the present embodiment is a step of increasing a resolution of the interface of the subject in the scan image obtained by obtaining the subject using the blurring function measured in the blurring function measuring step S100 described above, and includes a step S210 of interpolating the scan image and a step (not illustrated) of restoring the interpolated scan image.

In the step S210 of interpolating the scan image, the scan image is interpolated to correspond to the oversampling interval of the slit image. Since the synthesized LSF oversampled at the sampling interval of Δx/4 in the measurement of the blurring function according to the slit image is measured, it is necessary to enlarge the scan image by the oversampling interval in order to apply the oversampled blurring function to the scan image. Therefore, the interpolation of the scan image according the aforementioned embodiment is to enlarge the scan image four times.

In the step (not illustrated) of restoring the interpolated scan image, the scan image interpolated in the step S210 of interpolating the scan image is restored using the blurring function such that the resolution of the interface of the subject increases. To be more specific, the step (not illustrated) of restoring the interpolated scan image may include a step S220 of limiting and restoring an interface frequency, a CT image reconstructing step S230, a step S240 of detecting the interface, and a step S250 of calculating surface data.

In the step S220 of limiting and restoring the interface frequency, since a desired result of the present embodiment is an image of the interface of the subject, the scan image is restored by limiting a frequency of the subject to a frequency of a boundary portion including the interface of the subject.

When the restoration of the image is applied to typical images, there is a feature that, because the subject generally includes infinite frequency information, aliasing inevitably incurs, and thus noise increases. When the image is restored by limiting the frequency of the subject to the frequency of the boundary portion in order to acquire a clear image of the interface required in the present embodiment by removing this feature, it is possible to avoid the increase of the noise and the aliasing.

Furthermore, in the present embodiment, the scan image may be a CT scan image acquired by CT. In this case, the scan image restoring step S200 may further include the step S230 of reconstructing the restored scan image to a CT image. Therefore, in the CT image reconstructing step S230, sampling increases, and the restored image is reconstructed to the CT image having a desired resolution. The image reconstruction in the present embodiment may downscale and reconstruct the image enlarged in the step S210 of interpolating the scan image to an image according to the pixel interval prior to the interpolation, and a method therefor may be dependent on the desired resolution.

The step S240 of detecting the interface is a step of detecting the interface from the image reconstructed in the CT image reconstructing step S230. The interface in the present embodiment is preferably a surface by which an area of interest to be obtained by an image obtaining device and a background area other than the area of interest. The interface in the present embodiment is preferably detected using a Sobel mask.

The interface is preferably present at a point at which brightness of the pixel in the image varies from a low value to a high value and vice versa. Thereby, the image can represent a shape, size, and texture of an object. Therefore, the interface is detected to acquire information about the interface of the image using these characteristics and, more particularly, to find a pixel corresponding to the interface.

In one embodiment, the detection of the interface may be performed by detecting a variation in brightness. The Sobel mask may be used to detect the variation. The Sobel mask detects interfaces in all directions, is robust to noise, and is more sensitive to diagonal interfaces than vertical and horizontal interfaces. As a size of the mask increases, a thickness of the interface increases, and thus the interface is made clear. In addition, the mask may be the vertical mask, the horizontal mask, or a Laplacian mask according to secondary differentiation.

In the step S250 of calculating surface data, the surface data is calculated on the basis of results of detecting the interfaces. To utilize the results of detecting the interfaces as the surface data, the surface data in the present embodiment may have a STereoLithography (STL) file format. The surface data should be converted into a file format to be able to recognize a modeled data file in various pieces of equipment. The STL file format is a file format having an STL extension used in an STL system.

The STL file format is a file format in which a surface of a three-dimensional object is polygonized to small and large triangular faces that are polygonal faces so as to recognize various faces from angled faces to curved faces.

A device 100 for restoring a scan image, which performs the method for restoring a scan image according to the embodiment of the present invention will be described with reference to the drawings.

Figure 11:
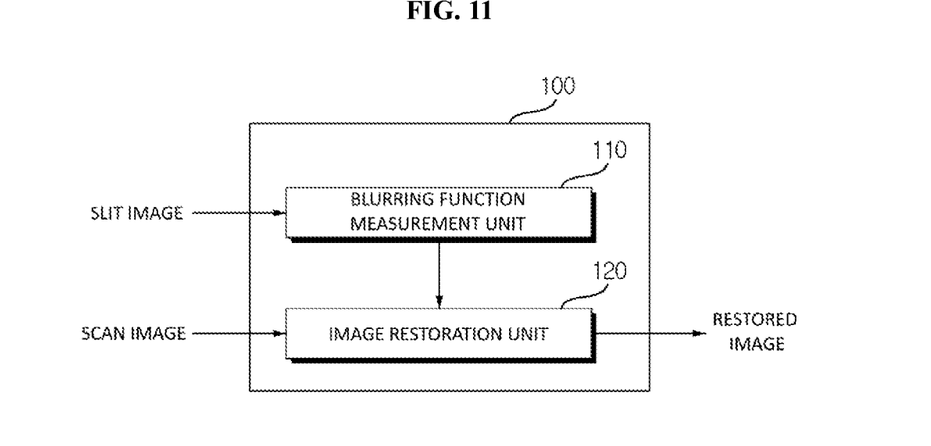
FIG. 11 is a block diagram illustrating a device for restoring a scan image according to an embodiment of the present invention.

Referring to FIG. 11, the device 100 for restoring a scan image in the present embodiment includes a blurring function measurement unit 110 and an image restoration unit 120. The blurring function measurement unit 110 receives a slit image obtained through a slit that is vertically or horizontally inclined at a predetermined angle, and measures a blurring function oversampled according to the predetermined angle. The image restoration unit 120 restores a scan image obtained by obtaining a subject using the measured blurring function such that a resolution of an interface of the subject is increased.

Figure 12:
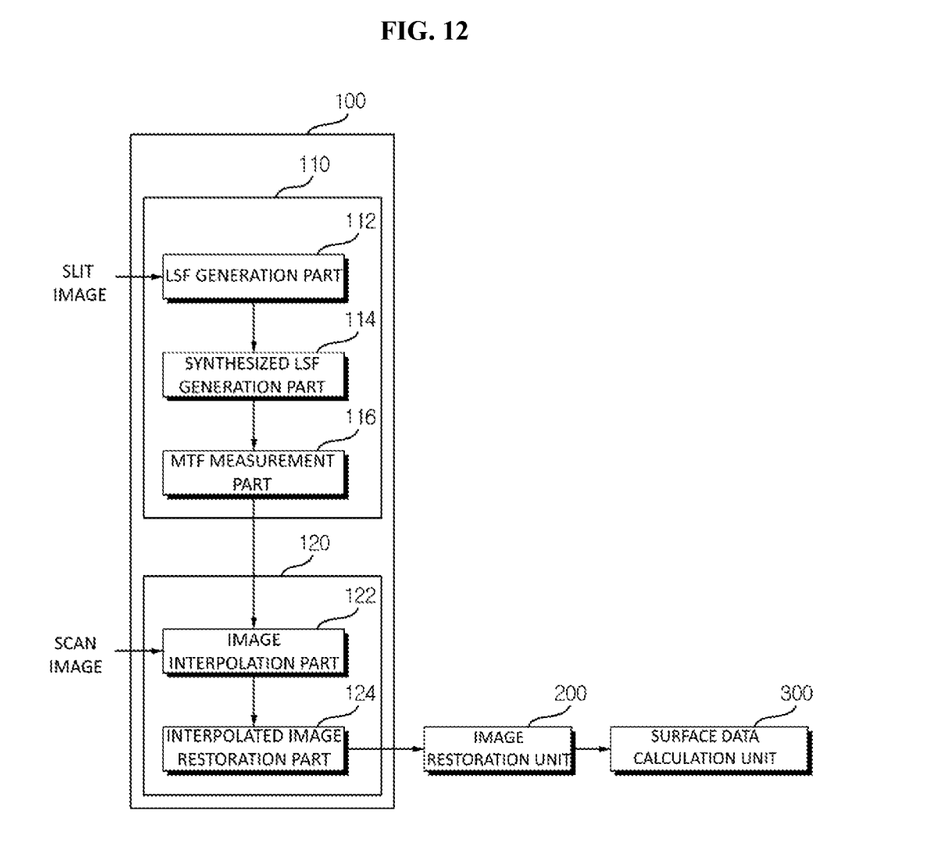
FIG. 12 is a block diagram illustrating a detailed configuration of the device for restoring the scan image of FIG. 11.

To be more specific, referring to FIG. 12, the blurring function measurement unit 110 includes an LSF generation part 112), a synthesized LSF generation part 114, and an MTF measurement part 116. The LSF generation part 112 generates LSFs for a plurality of alignments with respect to the slit image wherein the LSFs are sampled according to a pixel interval of the slit image and are composed of digital values.

The synthesized LSF generation part 114 synthesizes and generates the plurality of LSFs according to an interval obtained by dividing the pixel interval by the number N of pixels between the plurality of alignments.

The MTF measurement part 116 performs Fourier transform of the LSFs to OTFs, and measures MTFs using the transformed OTFs. In the present embodiment, the blurring function measurement unit 110 performs the aforementioned step of measuring the blurring function, and detailed description thereof will be omitted.

The image restoration unit 120 includes an image interpolation part 122 and an interpolated image restoration part 124. The image interpolation part 122 interpolates the scan image to correspond to the oversampling interval of the slit image. The interpolated image restoration part 124 restores the interpolated scan image using the blurring function measured by the blurring function measurement unit. The restoring process also corresponds to the aforementioned scan image restoring step, and thus detailed description thereof will be omitted.

Furthermore, the device for restoring the scan image may further include an image reconstruction unit 200 that reconstructs the restored scan image to be a CT image when the scan image in the present embodiment is a CT scan image acquired by CT, and a surface data calculation unit 300 that calculates surface data by detecting the interface from the reconstructed CT image.

In the CT that applies the image restoration by increasing the sampling according to the method and device for restoring the scan image, it is possible to secure a precise image for computer-aided design (CAD)/computer-aided manufacturing (CAM), which is additionally used in a system used when a patient is actually diagnosed, and thereby to apply the image restoration without additional expenses and equipment.

Meanwhile, the method for restoring the scan image in the present invention may be realized with a code which a computer can read from a computer-readable recording medium. The computer-readable recording medium includes all types of recording devices in which data that can be read by a computer system is stored.

Examples of the computer-readable recording medium include read-only memories (ROMs), random access memories (RAMs), CD-ROMs, magnetic disks, floppy disks, optical data storages, and so on. Further, the computer-readable recording medium can be distributed to computer systems connected over a network and be stored and executed in a distributed way with computer-readable codes. Functional programs, codes, and code segments for realizing the present invention can be easily inferred by programmers of the technical field of the present invention.

Although the preferred embodiments of the present invention have been disclosed for illustrative purposes, those skilled in the art will appreciate that various modifications, additions and substitutions are possible, without departing from the scope of the invention as disclosed in the accompanying claims.

Accordingly, the embodiments disclosed in the present invention and the accompanying drawings are for illustration only, but not meant to limit the technical idea of the invention. The scope of the technical idea of the invention is not limited by these embodiments and the accompanying drawings. The scope of the present invention should be interpreted by the claims, and all technical ideas within the range equivalent thereto should be interpreted as being within the scope of the invention.

The invention claimed is:

1. A method for restoring a scan image from an image system using X-rays, the method comprising the steps of:
   obtaining a slit image through a slit inclined at a predetermined angle;
   measuring a blurring function oversampled with respect to the slit image;
   obtaining the scan image of a subject; and
   restoring the scan image to increase a resolution of an interface of the subject using the measured blurring function,
   wherein the step of measuring the blurring function includes the sub-steps of:
   generating line spread functions (LSFs) with respect to a plurality of alignments sampled with respect to the slit image; and
   measuring a modulation transfer function (MTF) as the blurring function of the slit image using the plurality of LSFs.

2. The method as set forth in claim 1, wherein the plurality of alignments is composed of digital values sampled with respect to the slit image according to a pixel interval of the slit image; and.

3. The method as set forth in claim 2, wherein the step of measuring the blurring function further includes the sub-step of synthesizing the plurality of generated LSFs according to the angle and the pixel interval of the slit image to generate a synthesized LSF, and the sub-step of measuring the MTF includes measuring the MTF using the synthesized LSF.

4. The method as set forth in claim 3, wherein the sub-step of generating the synthesized LSF includes synthesizing and generating the plurality of LSFs according to an interval obtained by dividing the pixel interval by the number (N) of the pixels between the plurality of alignments.

5. The method as set forth in claim 1, wherein the step of restoring the scan image includes the sub-steps of:
   interpolating the scan image to correspond to an interval of sampling the slit image; and
   restoring the interpolated scan image using the measured blurring function.

6. The method as set forth in claim 1, wherein the sub-step of measuring the MTF includes transforming the LSFs to optical transfer functions (OTFs) using Fourier transform, and measuring the MTF using the transformed OTFs.

7. The method as set forth in claim 6, wherein the measured MTF is an absolute value of the transformed OTF.

8. The method as set forth in claim 1, wherein the step of restoring the scan image includes the sub-step of limiting a frequency of the subject to a frequency of a boundary portion including the interface of the subject to restore the scan image.

9. The method as set forth in claim 1, wherein the scan image is a computed tomography (CT) scan image acquired by CT, and the method of restoring the scan image further includes the step of reconstructing the scan image to a CT image.

10. The method as set forth in claim 9, further comprising the step of calculating surface data by detection of the interface from the reconstructed CT image.

11. The method as set forth in claim 1, wherein the angle of the slit inclined in the vertical or horizontal direction ranges from 2 to 3°.

12. A method for restoring a scan image from an image system using X-rays, the method comprising the steps of:
   obtaining a slit image through a slit inclined at a predetermined angle;
   measuring a modulation transfer function (MTF) using line spread functions (LSFs) for a plurality of alignments composed of digital values sampled with respect to the slit image;
   obtaining the scan image of a subject;
   interpolating the scan image to correspond to an interval of sampling the slit image; and
   restoring the interpolated scan image according to an interface a predetermined frequency using the modulation transfer function.

* * * * *